United States Patent [19]

Thottathil

[11] Patent Number: 4,885,380

[45] Date of Patent: Dec. 5, 1989

[54] PROCESS FOR PREPARING PHOSPHONYLOXYACYL AMINO ACIDS AND DERIVATIVES THEREOF

[76] Inventor: John K. Thottathil, 585 Flock Rd., Trenton, N.J. 08690

[21] Appl. No.: 237,490

[22] Filed: Aug. 26, 1988

Related U.S. Application Data

[62] Division of Ser. No. 839,256, Mar. 13, 1986, abandoned.

[51] Int. Cl.$^4$ .............................................. C07F 9/21
[52] U.S. Cl. ...................................... 558/83; 548/113
[58] Field of Search ........................................ 558/83

[56] References Cited

U.S. PATENT DOCUMENTS

| | | | |
|---|---|---|---|
| 4,168,267 | 9/1979 | Petrillo | 548/413 |
| 4,427,665 | 1/1984 | Karanewsky et al. | 548/414 |
| 4,452,790 | 6/1984 | Karanewsky et al. | 548/413 |
| 4,616,005 | 10/1986 | Karanewsky et al. | 548/414 |

FOREIGN PATENT DOCUMENTS 237264 9/1987 European Pat. Off. ............ 558/83

OTHER PUBLICATIONS

Baylis, et al, J. Chem. Soc. Perkin Trans. 1, 2845 (1984).
Kosolapoff et al, "Organic Phosphonous Compounds", Wiley–Interscience, N.Y. 1972, vol. 4, pp. 288 and 294–295 and vol. 7, p. 11.
Mehrotra, Can. J. Chem., 63, 663 (1985).
Ramirez, Tetrahedron 29, 3741 (1973).

*Primary Examiner*—Anton H. Sutto
*Attorney, Agent, or Firm*—Burton Rodney

[57] ABSTRACT

A process is provided for preparing phosphonyloxyacylamino acids and derivatives thereof having the structure $$R_1-\overset{O}{\underset{OR_3}{\overset{\|}{P}}}-O-\overset{R_2}{\underset{R_{2'}}{\overset{|}{C}}}-\overset{O}{\overset{\|}{C}}-X$$

wherein

X is $H_2C\overset{R_4}{\underset{}{\diagup}}CH_2$, etc. (structures shown)

which includes the steps of treating a phosphonic acid dichloride of the structure $$R_1-\overset{O}{\underset{Cl}{\overset{\|}{P}}}-Cl$$

with an α-hydroxy acid of the structure $$\underset{HO}{\overset{HO}{\diagdown}}\overset{R_2}{\underset{}{\diagup}}\overset{}{\underset{O}{C}}-R_{2'}$$

in the presence of base such as triethylamine at reduced temperatures to form the cyclic mixed anhydride of the structure (cyclic mixed anhydride structure shown)

(which is a new intermediate) and reacting the cyclic mixed anhydride with an amino acid or ester of the structure

HX in the presence of base such as triethylamine produces the ACE inhibitor compound $$R_1-\overset{O}{\underset{OH}{\overset{\|}{P}}}-O-\overset{R_2}{\underset{R_{2'}}{\overset{|}{C}}}-\overset{O}{\overset{\|}{C}}-X$$

(Abstract continued on next page.)

In an alternative process, the cyclic anhydride is quenched with water to form the diacid

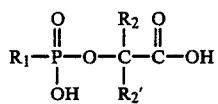

which is treated with a condensing agent such as dicyclohexyl carbodiimide (DCC), 1,1-carbonyldiimidazole (CDI) or thionyl chloride followed by quenching with the amion acid

HX produces the above ACE inhibitor compound.

In another variation of the process of the invention, the above cyclic anhydride is treated with an alcohol of the structure

R$_3$OH to form the phosphonic acid diester

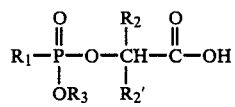

which may be coupled with the amino acid or ester

HX to form the ACE inhibitor

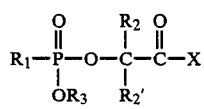

5 Claims, No Drawings

PROCESS FOR PREPARING PHOSPHONYLOXYACYL AMINO ACIDS AND DERIVATIVES THEREOF

This is a division of application Ser. No. 839,256 filed Mar. 13, 1986, now abandoned.

FIELD OF THE INVENTION

The present invention relates to a process for preparing phosphonyloxyacylamino acids and derivatives, such as disclosed in U.S. Pat. No. 4,452,790, which are angiotensin converting enzyme inhibitors and thus are useful in treating hypertension.

BACKGROUND OF THE INVENTION

Phosphoric acid and their derivatives have become increasingly important in recent years due to their useful biological properties, such as their ability to lower blood pressure due to their angiotensin converting enzyme inhibition activity, such as disclosed in U.S. Pat. No. 4,316,896 to Thorsett et al and U.S. Pat. Nos. 4,168,267 to Petrillo and 4,452,790 to Karanewsky et al.

The Arbuzov reaction of trialkylphosphites with suitable alkylating agents is a commonly used method for the preparation of phosphonic acid esters but it often requires high temperatures, neat reaction mixtures and other strong impractical conditions. Additionally, complex product mixtures are common due to competitive alkylation by alkyl halide side products generated in the reaction. E. K. Baylis, C. D. Campbell and J. G. Dingwall, J. Chem. Soc. Perkin Trans. 1, 2845 (1984); G. M. Kosolapoff and L. Maier, "Organic Phosphonous Compounds", Wiley-Interscience, N.Y. 1972, Vol. 4, pp. 288 and 294–295 and Vol. 7, page 11; R. N. Mehrotra, Can. J. Chem., 63, 663 (1985); and C. F. Guichard, Chem. Ber., 32 1572 (1899) disclose the oxidation of phosphonous acids or its esters to phosphonic acids or its esters which often requires strong, poisonous, expensive and gaseous reagents.

U.S. Pat. No. 4,452,790 to Karanewsky et al discloses phosphonyl hydroxyacyl amino acid derivatives having the structure $$R_1-\underset{\underset{OR_3}{|}}{\overset{\overset{O}{\|}}{P}}-O-\underset{\underset{}{|}}{\overset{R_2}{\underset{}{C}H}}-\overset{\overset{O}{\|}}{C}-X$$

wherein $R_1$ includes lower alkyl, aminoalkyl, haloalkyl, aryl, arylalkyl, cycloalkyl and cycloalkylalkyl; $R_2$ includes H, lower alkyl, aminoalkyl, aryl, arylalkyl, cycloalkyl and cycloalkylalkyl;

$R_3$ includes H, lower alkyl and arylalkyl; and

X is $$H_2C\underset{\underset{-N-\underset{H}{\overset{|}{C}}-COOR_6,}{}}{\overset{\overset{R_4}{|}}{\underset{CH_2}{}}} \quad H_2C\underset{\underset{-N-\underset{H}{\overset{|}{C}}-COOR_6,}{}}{\overset{\overset{S\underset{}{\times}S}{}}{\underset{CH_2}{}}}$$

(L)

-continued $$-N\underset{\underset{COOR_6,}{|}}{\overset{}{\underset{C}{}}}\phantom{XX} -N-\underset{\underset{H}{|}}{\overset{}{C}}-COOR_6 \text{ or}$$

$$-N-\underset{\underset{H}{|}}{\overset{}{C}}-COOR_6$$

wherein $R_4$ includes H, lower alkyl, halogen, keto, OH, amino, aryl, arylalkyl, lower alkoxy or arylalkyloxy; and $R_6$ includes H, lower alkyl, arylalkyl, alkali metal salt such as Li, Na or K, benzhydryl or $$-\underset{\underset{R_{15}}{|}}{C}H-O-\overset{\overset{O}{\|}}{C}-R_{16}$$

wherein $R_{15}$ is H, lower cycloalkyl or phenyl, and $R_{16}$ is H, lower alkyl, lower alkoxy, phenyl, or $R_{15}$ and $R_{16}$ taken together are $-(CH_2)_2-$, $-(CH_2)_3-$, $-CH=CH-$ or (phenyl ring)

In the above patent, Karanewsky et al teach that the above compounds may be prepared treating a phosphonic acid $$R_1-\underset{\underset{OH}{|}}{\overset{\overset{O}{\|}}{P}}-OH$$

with a chlorinating agent such as phosphorus pentachloride to form the dichloride $$R_1-\underset{\underset{Cl}{|}}{\overset{\overset{O}{\|}}{P}}-Cl$$

which is treated with an alcohol $$HO-\underset{\underset{}{|}}{\overset{R_2}{C}H}-CO_2alkyl$$

in the presence of triethylamine, followed by an alcohol $R_3OH$ to form

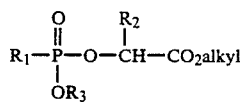

which is hydrolyzed by treatment with strong base to form the corresponding acid

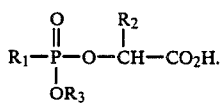

The above acid or its activated form is then coupled with an imino or amino acid H-X.

In the above reaction, if $R_1$ is p-hydroxyphenylalkyl, di-hydroxyphenylalkyl, aminoalkyl, guanidinyl, mercaptoalkyl or imidazolyl, then the hydroxyl, amino, imidazolyl, mercaptan or guanidinyl function should be protected during the coupling reaction. Similarly, if $R_2$ is aminoalkyl, then the amino group should be similarly protected.

DESCRIPTION OF THE INVENTION

In accordance with the present invention, a mild simple rapid and efficient process is provided for directly preparing phosphonyloxyacylamino acids and derivatives thereof as disclosed in U.S. Pat. No. 4,452,790 to Karanewsky et al and which have the general formula I

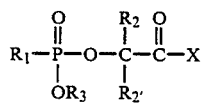

wherein

X is 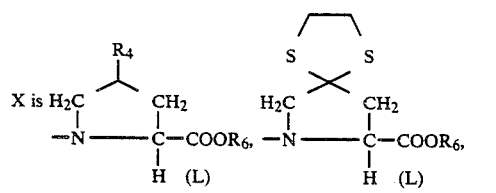

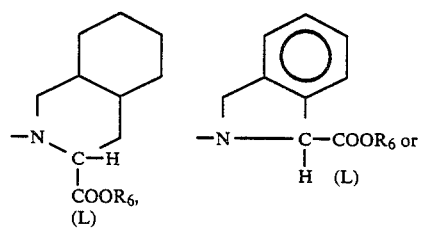

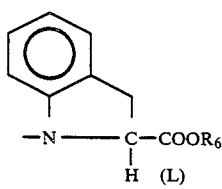

$R_1$ is lower alkyl, aminoalkyl, haloalkyl, aryl, aralkyl, cycloalkyl or cycloalkylalkyl;

$R_2$ is H, lower alkyl, aminoalkyl, aryl, aralkyl, cycloalkyl or cycloalkylalkyl;

$R_{2'}$ is H or lower alkyl;

$R_3$ is H, lower alkyl or aralkyl;

$R_4$ includes H, lower alkyl, halogen, keto, OH, amino, aryl, arylalkyl, lower alkoxy or arylalkyloxy; and $R_6$ includes H, lower alkyl, arylalkyl, alkali metal salt such as Li, Na or K, benzhydryl or

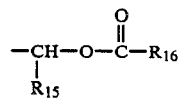

wherein $R_{15}$ is H, lower alkyl, cycloalkyl or phenyl, and $R_{16}$ is H, lower alkyl, lower alkoxy, phenyl, or $R_{15}$ and $R_{16}$ taken together are $-(CH_2)_2-$, $-(CH_2)_3-$, $-CH=CH-$ or

The process of the invention includes the steps of treating a phosphonic acid dichloride of the structure

 II dissolved in an inert solvent such as dry tetrahydrofuran, diethyl ether or dichloromethane and maintained at a reduced temperature of from about $-80°$ C. to about $-65°$ C. in the presence of base such as triethylamine, with an α-hydroxy acid of the structure

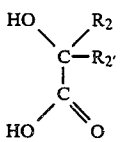 III dissolved in an inert solvent such as dry tetrahydrofuran, diethyl ether or dichloromethane, and maintained at a temperature of within the range of from about $-85°$ C. to about $-65°$ C. to form the cyclic mixed anhydride of the structure

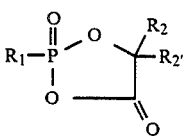 IV (which is a new intermediate), warming the reaction mixture to a temperature within the range of from about $-75°$ C. to about 25° C. and reacting the cyclic mixed anhydride with an imino or amino acid or ester of the structure

HX V in the presence of base such as triethylamine, to produce the ACE inhibitor compound

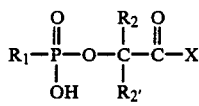  VI

The above process produces remarkably high yields especially in view of the formation of cyclic anhydride IV from homobifunctional compound II and heterobifunctional compound III and the chemospecific ring opening of IV to VI.

In an alternative process, the cyclic anhydride IV is quenched with water to form the diacid

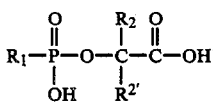  VII which is treated with a condensing agent or coupling agent such as dicyclohexylcarbodiimide (DCC), 1,1-carbonyldiimidazole (CDI) or thionyl chloride followed by quenching with the imino or amino acid or ester

H-X  V to produce the above ACE inhibitor compound VI.

In another variation of the process of the invention, the above cyclic anhydride IV is treated with an alcohol of the structure

R$_3$OH  VIII to form the phosphonic acid diester

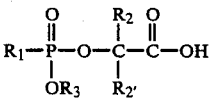  IX which may be coupled with the amino acid or ester

HX  V to form the ACE inhibitor

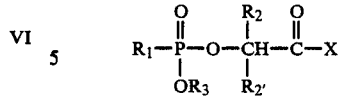  VIA employing coupling agents and procedures as set out herein with respect to the preparation of compound VI from acid VII.

The above reactions may be carried out without separating intermediates from the reaction vessels and employing readily available starting materials.

Where R$_2$ in the above starting materials is

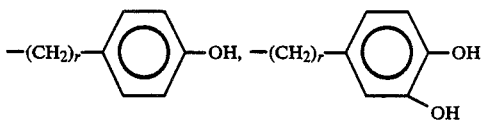

or or —(CH$_2$)$_r$—NH$_2$ (wherein r is 1 to 4), then the hydroxyl or amino function should be protected during the coupling or condensation reaction. Suitable protecting groups include benzyloxycarbonyl (also indicated by the designation "Z"), t-butoxycarbonyl (also indicated by the designation "BOC"), benzyl, benzhydryl, trityl, etc. The protecting group is removed by catalytic hydrogenolysis, treatment with acid, or other known methods following completion of the reaction.

Similarly, if in the above reactions, R$_1$ is aminoalkyl, then the amino group should be similarly protected, preferably by phthalidyl. The protecting groups is removed by treatment with hydrazine following completion of the reaction.

Novel intermediates and novel final products which are produced by carrying out the process of the invention and include

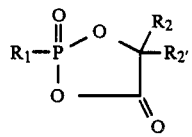  A

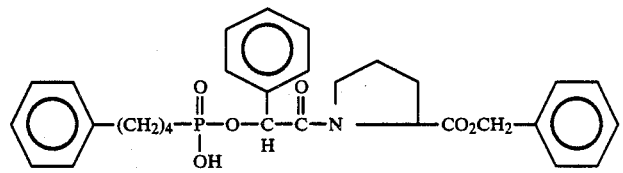  B.

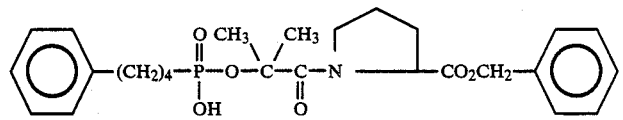  C.

DETAILED DESCRIPTION OF THE INVENTION

In carrying out the process of the invention to prepare compounds of formula VI, the dichloride starting material II will be reacted with the α-hydroxy acid III at a temperature of within the range of from about −85° C. to about −65° C. and preferably from about −75° C.

to about −70° C. for a period of from about 5 to about 1 hours and preferably from about 3 to about 2 hours, employing a molar ratio of II:III of within the range of from about 3:1 to about 0.5:1 and preferably from about 1.5:1 to about 0.7:1, and optimally about 1:1. The reaction is carried out in the presence of a base such as triethylamine, pyridine or N,N-dimethylamine employing a molar ratio of base:dichloride of within the range of from about 5:1 to about 1:1, and preferably from about 3:1 to about 1.5:1, and optimally about 2:1.

The resulting cyclic mixed anhydride IV need not be separated from the reaction mixture but may be warmed, as part of the reaction mixture, to a temperature of within the range of from about −75° C. to about 25° C. Anhydride IV is then reacted with the imino or amino acid or ester V (in the presence of a base such as triethylamine, pyridine or N,N-dimethylamine if V is used in the form of its acid salt such as the HCl salt) at a temperature within the range of from about 0° C. to about 35° C. and preferably from about 20° to about 28° C., employing a molar ratio of V:IV of within the range of from about 3:1 to about 0.5:1 and preferably from about 15:1 to about 0.7:1, and optimally about 1:1; while the base (where employed) will be employed in a molar ratio to V within the range of from about 3:1 to about 0.5:1 and preferably from about 1.5:1 to about 0.7:1.

In an alternative process of the invention described above, the cyclic mixture anhydride IV is quenched with water employing a molar ratio of water:IV is quenched with water employing a molar ratio of water:IV of within the range of from about 5:1 to about 0.5:1 and preferably from about 2:1 to about 0.7:1; and optimally about 1:1. The resulting acid VII is then reacted with coupling agent and acid or ester V employing a molar ratio of coupling agent:VII of within the range of from about 4:1 to about 0.5:1 and preferably from about 2:1 to about 0.7:1, and optimally about 1:1, and a molar ratio of V:VII within the range of from about 4:1 to about 0.5:1 and preferably from about 2:1 to about 0.7:1, and optimally about 1:1. The coupling reaction will be carried out at a temperature within the range of from about 0 to about 35° C. and preferably from about 20° to about 25° C. for a period of from about 1 to about 20 hours and preferably from about 2 to about 12 hours.

In the process wherein the cyclic mixed anhydride IV is treated with alcohol VIII, the alcohol VIII will be employed in a molar ratio to anhydride IV (that is VIII:IV) of within the range of from about 4:1 to about 0.5:1 and preferably from about 2:1 to about 0.7:1, and optimally about 1:1, and the reaction will be carried out at a temperature within the range of from about 0° to about 35° C. and preferably from about 20° to about 25° C. for a period within the range of from about ½ to about 3 hours and preferably from about 1 to about 2 hours.

The resulting phosphonic acid diester IX will than be made to undergo a coupling reaction wherein it is reacted with acid or ester V in the presence of a coupling agent as exemplified above employing a molar ratio of V:IX of within the range of from about 4:1 to about 0.5:1 and preferably from about 2:1 to about 0.7:1, and optimally about 1:1, a molar ratio of coupling agent:IX of within the range of from about 4:1 to about 0.5:1 and preferably from about 2:1 to about 0.7:1, and optimally about 1:1, at a temperature within the range of from about 0° to about 30° C., and preferably from about 20° to about 25° C., for a period of from about 1 to about 20 hours, and preferably from about 2 to about 12 hours.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl" or "lower alkyl" as used throughout the specification either by itself or as part of a larger group, refers to groups having 1 to 10 carbon atoms which may include an aryl, amino, cycloalkyl or halo substituent. Alkyl groups having 1 to 4 carbon atoms are preferred.

The term "cycloalkyl", as used throughout the specification either by itself or as part of a larger group, refers to groups having 3 to 7 carbon atoms.

The term "alkoxy" or "alkylthio", as used throughout the specification either by itself or as part of a larger group, refers to groups having 1 to 8 carbon atoms. Alkoxy or alkylthio groups having 1 to 3 carbon atoms are preferred.

The term "arylalkyl" or "cycloalkylalkyl", as used throughout the specification either by itself or as part of a larger group, refers to an "alkyl" group as defined above containing an "aryl" or "cycloalkyl" substituent.

The term "halo" or "halogen" as used throughout the specification either by itself or as part of a larger group, refers to Cl, Br, F, I or $CF_3$.

Examples of α-hydroxy acids III useful as starting materials in carrying out the present invention include, but are not limited to, the L-configuration $$\begin{array}{c} HO \diagdown \quad / R_2 \\ (L) \quad C-R_{2'} \\ | \\ C \\ HO \diagup \quad \diagdown O \end{array} \quad III$$

| $R^2$ | $R_{2'}$ |
|---|---|
| H | H |
| $CH_3$ | $CH_3$ |
| $C_4H_9$ | $C_2H_5$ |
| $C_5H_{11}$ | $n$-$C_4H_9$ |
| $CH_2C_6H_5$ | |
| $C_7H_5$ | |
| $(CH_2)_3$—Cl | |
| $(CH_2)_4$—NHCOCH$_2$C$_6$H$_5$ $\underset{O}{\overset{\parallel}{}}$ | |
| $(CH_2)_4$—NHCOC(CH$_3$)$_3$ $\underset{O}{\overset{\parallel}{}}$ | | with the latter two compounds being preferred.

Examples of dichlorides II useful as starting materials in carrying out the present invention include, but are not limited to,

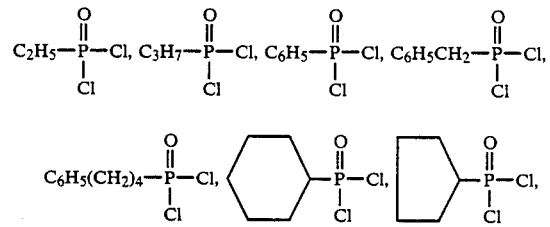

-continued

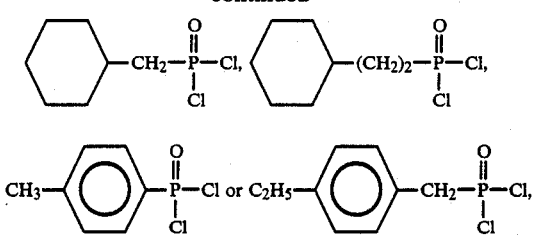

with

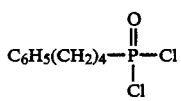

or esters thereof being preferred.

Examples of acids or esters V useful in carrying out the present invention include, but are not limited to

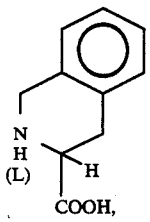

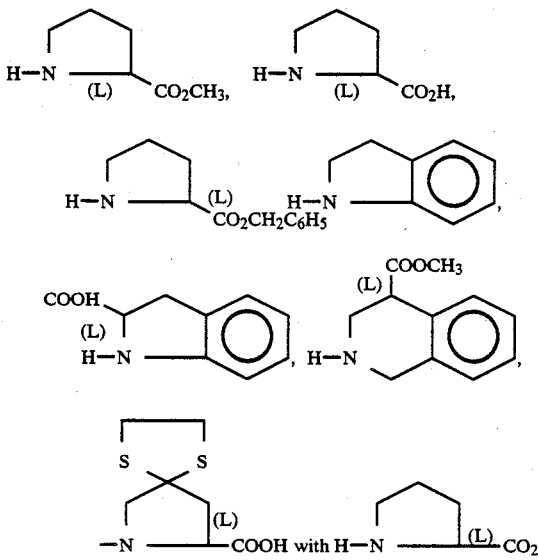

wherein $R_6$ is H or benzyl being preferred.

The starting dichloride compounds may be prepared as described in U.S. Pat. No. 4,452,790 to Karanewsky et al.

The compounds of formulas B and C form basic salts with various inorganic and organic bases which are also included with the scope of the invention. Such salts include ammonium salts, alkali metal salts, like Li, Na and K salts, alkaline earth metal salts like calcium and magnesium salts, salts with organic bases, e.g., dicyclohexylamine salt, benzathine, N-methyl-D-glucamine, hydrabamine sals, salts with amino acids like arginine, lysine and the like. The non-toxic physiologically acceptable salts are preferred, although other salts are also useful, e.g., in isolating or purifying the products. The salts are formed using conventional techniques.

As shown above, the amino or imino acid or ester portion of the molecule of the products of formula I represented by X is in the L-configuration. Depending upon the definition of $R_1$ other asymmetric center may be present in the phosphonyl sidechain. Thus, some of the compounds can accordingly exist in diastereoisomeric forms or in mixtures thereof. The above-described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_4$ substituent in the starting material.

The compounds of formula B and C and the corresponding acids thereof, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood pressure, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→ (renin)→angiotensin I→angiotensin II sequence by inhibiting angiotensin converting enzyme and reducing or eliminating the formation of the pressor substance angiotensin II. Thus, by the administration of a composition containing one (or a combination) of the compounds of this invention, angiotensin dependent hypertension in a species of mammal (e.g., humans) suffering therefrom is alleviated. A single dose, or preferably two or four divided daily doses, provided on a basis of about 0.1 to 100 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 350 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formulas B and C can be formulated for use in the reduction of blood pressure in compositions such as tablets, capsules or elixirs for oral administration or in sterile solutions or suspensions for parenteral administration. About 10 to 500 mg of a compound of formulas B and C is compounded with physiologically acceptable vehicle, carrier, excipient, binder, preservatives, stabilizer, flavor, etc., in a unit dosage form as called for by accepted pharmaceutical practice. The amount of active substance in these compositions or preparations is such that a suitable dosage in the range indicated is obtained.

The following examples are illustrative and present preferred embodiments of the invention. Temperatures are given in degrees centigrade. AG-50W-X8 refers to a crosslinked polystyrenedivinylbenzene sulfonic acid cation exchange resin. HP-20 refers to a porous cross-linked polystyrenedivinyl benzene polymer resin.

EXAMPLE 1

(S)-1-[6-Amino-2-[[hydroxy(4-phenylbutyl)phosphinyl]oxy]-1-oxohexyl]-L-proline

A solution of 4-phenylbutylphosphonyl dichloride (prepared as described in U.S. Pat. No. 4,452,790) (50.0 gm, 0.199 mole) in tetrahydrofuran (THF) (1.2 L) was cooled to $-75°$ C. and triethylamine (63.0 ml, 0.45 mole) was added to the solution. A solution of the (S)-2-hydroxy-6-[(benzyloxycarbonyl)amino]hexanoic acid (56.0 gm, 0.199 mole) in THF (350 ml) was added dropwise to the dichloride solution with vigorous stirring while keeping the internal temperature $\sim -75°$ C. After the addition was over (2 hours), the mixture was stirred for 2 hours at $-78°$ C. and allowed to warm to ambient temperature in 1 hour time and was stirred 1 hour more at ambient temperature to produce the mixed anhydride of the type IV.

Powdered proline (25.0 gm, 0.21 mole) was added to the reaction mixture in one lot and the mixture was stirred at ambient temperature for 12 hours. The residue obtained after standard extractive aqueous work up was dissolved in methanol (500 ml) and 18% Pd(OH)$_2$/charcoal (10.0 gm) was added to it. Hydrogen gas was bubbled through the solution for 1 hour. Filtration and methanol evaporation followed by crystallization from water-acetone produced the title compounds in 86% (75.0 gm) yield, m.p. 190°–195° C.

EXAMPLE 2

(S)-1-[6-(Benzyloxycarbonyl)amino-2-[[hydroxy(4-phenylbutyl)]phosphinyl]oxy]-1-hexanoic acid A solution of 4-phenylbutylphosphonyl dichloride (prepared as described in U.S. Pat. No. 4,452,790) (5.0 gm, 0.0199 mole) in tetrahydrofuran (THF) (100 ml) was cooled to $-75°$ C. and triethylamine (6.5 ml, 0.045 mole) was added to the solution. A solution of (S)-2-hydroxy-6-[(benzyloxycarbonyl)amino]hexanoic acid hydroxy acid (5.6 gm, 0.0199 mole) in THF (40 ml) was added dropwise to the dichloride solution with vigorous stirring while keeping the internal temperature $\sim -75°$ C. After the addition was over (2 hours), the mixture was stirred for 2 hours at $-78°$ C. and allowed to warm to ambient temperature in 1 hour time and was stirred 1 hour more at ambient temperature. Water (200 ml) was added and the usual extractive workup produced 9.0 gm of clear glossy solid, single spot on TLC (Rf=0.2, CH$_2$Cl$_2$:HOAc:MeOH, 18:1:1), 95% yield.

Analysis (for the amino acid obtained after deprotecting by hydrogenolysis) C$_{16}$H$_{26}$NO$_5$P.1.25 M.H$_2$O Calcd: C, 52.52; H, 7.85; N, 3.83; P, 8.36
Found: C, 52.49; H, 7.73; N, 3.73; P, 8.20

EXAMPLE 3

(S)-1-[6-Amino-2-[[hydroxy(4-phenylbutyl)-phosphinyl]oxy]-1-oxohexyl-L-proline

The procedure as described in Example 1 was employed except proline benzyl ester hydrochloride (50 gm, 0.199 mole) and triethylamine (32 ml, 0.2 mole) were used in place of proline. Final yield after hydrogenolysis and crystallization was 71.3 gm (81%). [α]$_D$= −46.2, HI=99.03%

Anal for C$_{21}$H$_{33}$O$_6$N$_2$P, 1.18M H$_2$O
Calcd: C, 54.63; H, 7.72; N, 6.07; P, 6.71
Found: C, 54.60; H, 7.76; N, 5.99; P, 6.60

EXAMPLE 4

(S)-[6-Benzyloxycarbonylamino-2-[[hydroxy(4-phenylbutyl)phosphinyl]oxy]-1-oxohexyl]-L-proline The diacid of Example 3 (7.37 gm, 0.015 moles) was dissolved in CH$_2$Cl$_2$ and the solution was cooled in an ice bath. To this stirring solution was added solid dicyclohexylcarbodiimide (DCC) (3.34 gm). The mixture was removed from the ice bath and was stirred for 45 minutes at room temperature. Solid proline (1.77 gm) was added over 1 hour and the reaction mixture was stirred for 20 hours at room temperature. Dicyclohexylurea (DCU) was filtered and CH$_2$Cl$_2$ was removed on a rotovap. This residue was redissolved in ethyl acetate (150 ml) and it was washed with 10% HCl acid and dried over anhydrous MgSO$_4$. Ethyl acetate was removed on a rotovap and dried for 1 hour in vacuo to give a glassy solid, 8.89 gm, (100%), as a single spot on TLC (CH$_2$Cl$_2$:HOAc:MeOH; 17:1.5:1.5).

Anal for the mono benzylamine salt C$_{36}$H$_{48}$N$_3$O$_8$P
Calcd: C, 63.40; H, 7.09; N, 6.16; P, 4.54
Found: C, 63.01; H, 6.89; N, 6.02; P, 4.30

EXAMPLE 5

(S)-1-[6-t-Butoxycarbonylamino-2-[[hydroxy(4-phenylbutyl)phosphinyl]oxy]-1-oxohexyl]-L-proline benzyl ester, 1-adamantanamine salt A solution of 4-phenylbutylphosphonyl dichloride (5.0 gm, 0.0199 mole) in tetrahydrofuran (THF) (110 ml) was cooled to $-75°$ C. and triethylamine (6.3 ml, 0.044 mole) was added to the solution. A solution of (S)-2-hydroxy-6-(t-butyloxycarbonylamino) hexanoic acid (5.0 gm, 0.0199 mole) in THF (40 ml) was added dropwise to the dichloride solution with vigorous stirring while keeping the internal temperature $\sim -75°$ C. After the addition was over (2 hours), the mixture was stirred for 2 hours at $-78°$ C. and allowed to warm to ambient temperature in 1 hour time and was stirred 1 hour more at ambient temperature to obtain the mixed cyclic anhydride of the type IV.

Powdered proline benzyl ester (5.0 gm, 0.02 mole) and triethylamine (3.2 ml, 0.022 mole) were added to the reaction mixture in one lot and the mixture was stirred at ambient temperature for 12 hours. The residue obtained after standard extractive aqueous work up was dissolved in ethylacetate (50 ml) and ether (100 ml) and 1-adamantanamine (3.3 gm) was added to it. Hexane (50 ml) was added to the mixture which was left in the cold room overnight. Filtration gave 12 gm (75%) of material, m.p. 125°–130° C.

EXAMPLE 6

(R)-1-[2-Phenyl-2-[[hydroxy(4-phenylbutyl)phosphinyl]oxy]-1-oxoethyl]-L-proline benzyl ester, 1-adamantanamine salt A solution of 4-phenylbutylphosphonyl dichloride (2.0 gm, 0.00797 mole) in tetrahydrofuran (THF) (35 ml) was cooled to −75° C. and triethylamine (2.5 ml, 0.0175 mole) was added to the solution. A solution of d-mandelic acid (1.2 g, 0.00797 mole) in THF (10 ml) was added dropwise to the dichloride solution with vigorous stirring while keeping the internal temperature ∼−75° C. After the addition was over (2 hours), the mixture was stirred for 2 hours at −78° C. and allowed to warm to ambient temperature in 1 hour time and was stirred for 1 hour more at ambient temperature to obtain the mixed cyclic anhydride of the type IV.

Powdered proline benzyl ester (2.1 gm, 0.00876 mole) was added to the reaction mixture in one lot and the mixture was stirred at ambient temperature for 12 hours. The residue obtained after standard extractive aqueous work up was dissolved in ethyl acetate (50 ml), treated with 1-adamantanamine (1.2 gm, 0.00797 mole) and diluted with hexane (50 ml) and left at room temperature overnight. The precipitate was filtered and vacuum dried to obtain 4.8 gm (87.8%) of the product, m.p. 204°–207° C.

Anal for $C_{37}H_{51}O_6N_2P$:
Calcd: C, 68.29; H, 7.9; N, 4.30; P, 4.76
Found: C, 69.19; H, 7.6; N, 3.94; P, 4.50

EXAMPLE 7

(S)-1-[3-Phenyl-2-[[hydroxy(4-phenylbutyl)phosphinyl]oxy]-1oxohexyl-L-proline benzyl ester A solution of 4-phenylbutylphosphonyl dichloride (2.0 gm, 0.00797 mole) in tetrahydrofuran (THF) (35 ml) was cooled to −75° C. and triethylamine (2.5 ml, 0.0175 mole) was added to the solution. A solution of L-(−)-3-phenyllactic acid (1.329 g, 0.00797 mole) in THF (10 ml) was added dropwise to the dichloride solution with vigorous stirring while keeping the internal temperature ∼−75° C. After the addition was over (2 hours), the mixture was stirred for 2 hours at −78° C. and allowed to warm to ambient temperature in 1 hour time and was stirred 1 hour more at ambient temperature. The mixture was found to contain the mixed cyclic anhydride of the type IV.

Powdered proline benzyl ester (2.1 gm, 0.0087 mole) and triethylamine (1.3 ml, 0.0088 mole) were added to the reaction mixture in one lot and the mixture was stirred at ambient temperature for 12 hours. The residue obtained after standard extractive aqueous work up was crystallized from ethyl acetate-hexane to obtain 3.76 gm (83%) of the product, m.p. 94°–96° C.

Anal for $C_{31}H_{36}O_6NP.1.2M\ H_2O$:
Calcd: C, 65.18; H, 6.78; N, 2.45; P, 5.42
Found: C, 65.21; H, 6.68; N, 2.32; P, 5.40

EXAMPLE 8

(S)-1-[3-Isopropyl-2-[[hydroxy(4-phenylbutyl)-phosphinyl]oxy]-1-oxopropyl]-L-proline benzyl ester, 1-adamantanamine salt A solution of 4-phenylbutylphosphonyl dichloride (2.0 gm, 0.00797 mole) in tetrahydrofuran (THF) (35 ml) was cooled to −75° C. and triethylamine (2.5 ml, 0.0175 mole) was added to the solution. A solution of L-(α)-hydroxyisocaproic acid (56.0 gm, 0.199 mole) in THF (350 ml) was added dropwise to the dichloride solution with vigorous stirring while keeping the internal temperature ∼−75° C. After the addition was over (2 hours), the mixture was stirred for 2 hours at −78° C. and allowed to warm to ambient temperature in 1 hour time and was stirred 1 hour more at ambient temperature. The mixture was found to contain the mixed cyclic anhydride of the type IV.

Powdered proline benzyl ester (2.1 gm, 0.0087 mole) and triethylamine (1.3 ml, 0.0088 mole) were added to the reaction mixture in one lot and the mixture was stirred at ambient temperature for 12 hours. The residue obtained after standard extractive aqueous work up was dissolved in 20 ml ethylacetate and treated with 1.2 gm of 1-adamantanamine to get 4.41 gm (82.9%) of the adamantanamine salt, m.p. 208°–212° C.

Anal for $C_{38}H_{55}O_6N_2P$:
Calcd: C, 68.44; H, 8.31; N, 4.2; P, 4.64
Found: C, 68.53; H, 8.45; N, 3.9; P, 4.7

EXAMPLE 9

(S)-1-[2-Methyl-2-[[hydroxy(4-phenylbutyl)phosphinyl]oxy]-1-oxoethyl]-L-proline benzyl ester, 1-adamantanamine salt A solution of 4-phenylbutylphosphonyl dichloride in tetrahydrofuran (THF) (35 ml) was cooled to −75° C. and triethylamine (63.0 ml, 0.45 mole) was added to the solution. A solution of lactic acid (0.72 g) in THF (100 ml) was added dropwise to the dichloride solution with vigorous stirring while keeping the internal temperature ∼−75° C. After the addition was over (2 hours), the mixture was stirred for 2 hours at −78° C. and allowed to warm to ambient temperature in 1 hour time and was stirred 1 hour more at ambient temperature. The mixture was found to contain the mixed cyclic anhydride.

Powdered proline benzyl ester (2.1 gm, 0.0087 mole) and triethylamine (1.3 ml, 0.0088 mole) were added to the reaction mixture in one lot and the mixture was stirred at ambient temperature for 12 hours. The residue obtained after standard extractive aqueous work up was dissolved in 20 ml ethyl acetate and treated with 1.2 gm of 1-adamantanamine to get 4.1 gm (82.4%) of the salt, m.p. 171°–176° C.

Anal for $C_{35}H_{49}O_6N_2P$:
Calcd: C, 66.99; H, 8.06; N, 4.43; P, 5.1
Found: C, 67.29; H, 7.91; N, 4.48; P, 4.96

EXAMPLE 10

1-[2,2-Dimethyl-2-[[hydroxy(4-phenylbutyl)phosphinyl]oxy]-1-oxoethyl]-L-proline benzyl ester, 1-adamantanamine salt A solution of 4-phenylbutylphosphonyl dichloride (2.0 gm, 0.00797 mole) in tetrahydrofuran (THF) (35 ml) was cooled to −75° C. and triethylamine (2.5 ml, 0.0175 mole) was added to the solution. A solution of isobutyric acid (0.86 gm, 0.008 mole) in THF (10 ml) was added dropwise to the dichloride solution with vigorous stirring while keeping the internal temperature ∼−75° C. After the addition was over (2 hours), the mixture was stirred for 2 hours at −78° C. and allowed to warm to ambient temperature in 1 hour time and was stirred 1 hour more at ambient temperature. The mixture was found to contain the mixed cyclic anhydride of the type IV.

Powdered proline benzyl ester (2.1 gm, 0.0087 mole) and triethylamine (1.3 ml, 0.0088 mole) were added to the reaction mixture in one lot and the mixture was stirred at ambient temperature for 12 hours. The residue obtained after standard extractive aqueous work up was dissolved in 20 ml ethyl acetate and treated with 1.2 gm 1-adamantanamine to get 3.2 gm of the salt (82%), m.p. 117°–122° C.

Anal for $C_{36}H_{51}O_6N_2P$:
Calcd: C, 67.69; H, 8.05; N, 4.37; P, 4.85
Found: C, 66.45; H, 8.19; N, 4.37; P, 5.0

EXAMPLE 11

(S)-1-[6-Benzyloxycarbonylamino-2-[methoxy(4-phenylbutyl)phosphinyl]oxy]-1-hexanoic acid A solution of 4-phenylbutyl phosphonyl dichloride (5 g, 0.199 mole) in THF (100 ml) was cooled to −78° C. under argon atmosphere and triethylamine (6.5 ml, 0.043 mole) was added to it. A white cloudy precipitate formed. To this solution was added (S)-2-hydroxy-6-[(benzyloxycarbonyl)amino]hexanoic acid (5.6 g) in 40 ml THF at −75° C. over 45 minutes time period. After the addition, the reaction was stirred for 2 hours at −78° C., the cooling bath was removed and the mixture was stirred at room temperature for 2 hours. Methanol (2 ml) was added to the reaction mixture and the mixture stirred for 15 minutes. TLC showed complete reaction. The reaction mixture was filtered under argon atmosphere and the filtrate was concentrated on a rotovap to get the title ester as a clear yellowish syrup, 9.0 gm (94.8%) single spot on TLC ($CH_2Cl_2$:HOAc:MeOH; 18:1:1), Rf=0.6.

EXAMPLE 12

(S)-1-[6-Benzyloxycarbonylamino-2-[methoxy(3-phenylpropyl)phosphinyl]oxy]-1-hexanoic acid Following the procedure of Example 11 except substituting 3-phenylpropylphosphonyl dichloride for the dichloride used in Example 11, the title compound is obtained.

EXAMPLES 13 to 50

Following the procedure of Example 1 and the corresponding process techniques described in the Specification except substituting for the 4-phenylbutylphosphonyl dichloride, the compound shown in Column I of Table A set out below, substituting for the α-hydroxy acid of Example 1, the α-hydroxy acid set out in Column II, the intermediate set out in Column III is obtained and substituting for proline, the amino acid derivative set out in Column IV, the ACE inhibitor shown in Column V is obtained.

TABLE A

| Ex. No. | Column I<br>$R_1-\overset{\overset{O}{\|}}{P}-Cl$<br>$\quad\;\; Cl$<br>$R_1$ | Column II<br>$\begin{array}{c}R_2\\HO-C-CO_2H\\H\end{array}$<br>$R_2$ | Column III<br>(structure with $R_1$, $R_2$)<br>$R_1 \quad R_2$ | Column IV<br>XII | Column V<br>(structure)<br>$R_1 \quad R_2 \quad X$ |
|---|---|---|---|---|---|
| 13. | $H_3C-(CH_2)_2-$ | $-C_3H_7$ | as per Col. I / as per Col. II |  | as per Col. I / as per Col. II / as per Col. IV |
| 14. | $H_3C-$ | $-CH_3$ | |  | |
| 15. | $H_5C_2-$ | $-H$ | |  | |
| 16. | $C_6H_5$ | $-CH_3$ | |  | |
| 17. | 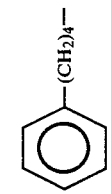$-(CH_2)_4-$ | $BOC-HN(CH_2)_2-$ | |  | |

TABLE A-continued

| Ex. No. | Column I $R_1\text{-}\overset{O}{\underset{Cl}{P}}\text{-}Cl$ $R_1$ | Column II $\underset{R_2}{\overset{R_2}{HO-C-CO_2H}}$ | Column III $R_1\text{-}\overset{O}{P}\overset{O}{\underset{O}{\diagdown}}\overset{R_2}{\underset{R_2}{C}}\overset{O}{\diagdown}$ $R_1 \quad R_2 \quad x$ | Column IV XII | Column V $R_1\text{-}\overset{O}{\underset{OH}{P}}\text{-}O\text{-}\overset{R_2}{\underset{R_2}{CH}}\text{-}\overset{O}{C}\text{-}X$ $R_1 \quad R_2 \quad X$ |
|---|---|---|---|---|---|
| 18. | (CH₂)₃— (phenyl) | —CH₃ | | decahydroisoquinoline-CH(COOCH₂Ph)(L) | |
| 19. | CH₂— (p-tolyl) | —(CH₂)₂—(phenyl) | | dithiolane-CH₂-N-CH(COOCH₂Ph)(H)(L) | |
| 20. | CH₂— (p-methoxyphenyl) | —(CH₂)₄NHCOCH₂—(phenyl) | | piperidine-CH(COOCH₂Ph)(H)(L) | |
| 21. | (CH₂)₂— (p-fluorophenyl) | —CF₃ | | piperidine-CH(COOCH₂Ph)(H)(L) | |

TABLE A-continued

| Ex. No. | Column I $R_1$ | Column II $R_2$ | Column III x | Column IV XII | Column V X |
|---|---|---|---|---|---|
| 22. | 2-Cl-C$_6$H$_4$-(CH$_2$)$_4$- | —CH$_3$ | | N-substituted with 2-Cl-benzyl group; —CH(COOCH$_2$C$_6$H$_5$)H (L) | |
| 23. | 4-(H$_3$CS)-C$_6$H$_4$-CH$_2$- | —H | | N-substituted with 2-(COOC(CH$_3$)$_3$)-benzyl (L), H | |
| 24. | cyclohexyl-(CH$_2$)$_4$- | —CH$_3$ | | N-(piperidinyl-type)—CH(COOCH$_2$C$_6$H$_5$)H (L) | |
| 25. | cyclopentyl-CH$_2$- | —CH$_3$ | | N-(dithiaspiro)—CH(COOCH$_2$C$_6$H$_5$)H (L) | |

TABLE A-continued

| | Column I | Column II | Column III | Column IV | Column V |
|---|---|---|---|---|---|
| | $R_1\text{-}\underset{Cl}{\underset{\|}{\overset{O}{\overset{\|}{P}}}}\text{-}Cl$ | $\underset{R_2}{\underset{\|}{HO\text{-}\overset{R_2}{\overset{\|}{C}}\text{-}CO_2H}}$ | (structure III with $R_1, R_2$) | XII | (structure V with $R_1, R_2, X$) |
| Ex. No. | $R_1$ | $R_2$ | | | |
| 26. | $H_3C\text{-}(CH_2)_6\text{-}$ | $-CH_3$ | | HO—[CH₂-CH(N-)-CH₂-CH(COOCH₂Ph)(H)] (L) | |
| 27. | $H_3C\text{-}(CH_2)_2\text{-}$ | $-CH_3$ | | [benzo-fused ring with CH₂-N-, CH-COOCH₂Ph (L), H] | |
| 28. | Ph— | $-CH_3$ | | $SCH_3$—[CH-CH₂-N-, with CH-COOC(CH₃)₃ (L), H] | |
| 29. | Ph-CH₂— | $-H$ | | Cl—[CH-CH₂-N-, with CH-COOCH₂Ph (L), H] | |

TABLE A-continued

| Ex. No. | Column I R₁ | Column II R₂ | Column III | Column IV XII | Column V |
|---|---|---|---|---|---|
| 30. | phenyl-(CH₂)₂— | —CH₃ | | 2-benzyl-phenyl substituted, N—CH(COOCH₂Ph)(L)—H | |
| 31. | phenyl-(CH₂)₄— | —CH₃ | | CH₃-CH(CH₂)—, N—CH(COOCH₂Ph)(L)—H | |
| 32. | phenyl-(CH₂)₆— | —CH₃ | | O=C(CH₂)—, N—CH(COOCH₂Ph)(L)—H | |
| 33. | 3,5-(H₃CO)₂-C₆H₃-(CH₂)₄— | —CH₃ | | N₃—CH(CH₂)—, N—CH(COOCH₂Ph)(L)—H | |

TABLE A-continued

| Ex. No. | Column I<br>$R_1-\overset{\overset{O}{\|\|}}{P}-Cl$<br>$\|$<br>$Cl$<br>$R_1$ | Column II<br>$\overset{R_2}{\underset{H}{\|}}$<br>$HO-C-CO_2H$<br>$\|$<br>$R_2$ | Column III<br>$R_1-\overset{O}{\overset{\|\|}{P}}\overset{O}{\underset{O}{\diagdown}}\overset{R_2}{\underset{R_2}{\diagup}}\overset{O}{\underset{x}{\|\|}}$<br>XI | Column IV<br>XII | Column V<br>$R_1-\overset{\overset{O}{\|\|}}{P}-O-\overset{R_2}{\underset{R_2}{\overset{\|}{C}}}H-\overset{O}{\overset{\|\|}{C}}-X$<br>$\|$<br>$OH$<br>$R_1 \quad R_2 \quad X$ |
|---|---|---|---|---|---|
| 34. | 4-Cl-C$_6$H$_4$-(CH$_2$)$_3$- | —CH$_3$ | | $\underset{N(CH_3)_2}{\overset{}{\diagdown}}\overset{}{\underset{-N}{\diagup}}\overset{COOCH_2-C_6H_5}{\underset{H}{\overset{\|}{C}}}\text{(L)}$ | |
| 35. | 4-H$_3$C-C$_6$H$_4$-(CH$_2$)$_6$- | —CH$_3$ | | $CH_2O-C=O$<br>$\|$<br>$NH$<br>$\diagdown\diagup$<br>$-N$<br>$\overset{COOCH_2-C_6H_5}{\underset{H}{\overset{\|}{C}}}\text{(L)}$ | |
| 36. | C$_6$H$_5$—(CH$_2$)$_4$— | —CH$_3$ | | $OH$<br>$\diagdown\diagup$<br>$-N$<br>$\overset{COOCH_2-C_6H_5}{\underset{H}{\overset{\|}{C}}}\text{(L)}$ | |
| 37. | tetrahydrothiopyranyl | —CH$_3$ | | $C_6H_5$<br>$\diagdown\diagup$<br>$-N$<br>$\overset{COOCH_2-C_6H_5}{\underset{H}{\overset{\|}{C}}}\text{(L)}$ | |

TABLE A-continued

| Ex. No. | Column I $R_1-\overset{\overset{O}{\|}}{P}-Cl$ $\overset{\|}{Cl}$ $R_1$ | Column II $R_2-\overset{R_2}{\underset{\|}{C}}-CO_2H$ $\overset{\|}{OH}\;\overset{\|}{H}$ $R_2$ | Column III $R_1-\overset{\overset{O}{\|}}{P}\overset{O}{\underset{O}{\diagdown}}\overset{R_2}{\underset{}{\diagup}}$ x | Column IV XII | Column V $R_1-\overset{\overset{O}{\|}}{P}-O-\overset{R_2}{\underset{\|}{CH}}-\overset{\overset{O}{\|}}{C}-X$ $\overset{\|}{OH}\;\;R_2$ |
|---|---|---|---|---|---|
| 38. | (thiophene)- | —CH$_3$ | | Ph-CH$_2$-CH((CH$_2$)$_2$)-CH$_2$-N-CH(COOC(CH$_3$)$_3$)(H) (L) | |
| 39. | (cyclohexyl)-CH$_2$— | —CH$_3$ | | Ph-CH$_2$-CH((CH$_2$)$_2$)-CH$_2$-N-CH(COOCH$_2$Ph)(H) (L) | |
| 40. | H$_3$C— | —CH$_3$ | | (4-F-Ph)-CH$_2$-CH-CH$_2$-N-CH(COOCH$_2$Ph)(H) (L) | |
| 41. | H$_5$C$_2$— | —CH$_3$ | | (cyclohexyl)-CH$_2$-CH-CH$_2$-N-CH(COOC(CH$_3$)$_3$)(H) (L) | |

TABLE A-continued

| Ex. No. | Column I $R_1-\overset{O}{\underset{Cl}{\overset{\|}{P}}}-Cl$ $R_1$ | Column II $HO-\underset{H}{\overset{R_2}{\underset{\|}{C}}}-CO_2H$ $R_2$ | Column III (x) | Column IV (XII) | Column V $R_1-\overset{O}{\underset{OH}{\overset{\|}{P}}}-O-\underset{R_2}{\overset{\|}{CH}}-\overset{O}{\overset{\|}{C}}-X$  $R_1 \quad R_2 \quad X$ |
|---|---|---|---|---|---|
| 42. | phenyl-(CH$_2$)$_2$— | —CH$_3$ | | —N[CH$_2$-CH((CH$_2$)$_2$-phenyl)-CH(COOCH$_2$phenyl)(L)-H] | |
| 43. | BOC—NH(CH$_2$)$_5$— | —CH$_3$ | | —N[CH$_2$-CH(cyclohexyl)-CH(COOC(CH$_3$)$_3$)(L)-H] | |
| 44. | Z—NH(CH$_2$)$_4$— | —CH$_3$ | | —N[CH$_2$-CH(CH$_2$-naphthyl)-CH(COOCH$_2$phenyl)(L)-H] | |

TABLE A-continued

| Ex. No. | Column I $R_1-\overset{\overset{O}{\|}}{P}-Cl$ $Cl$ $R_1$ | Column II $\overset{R_2}{\underset{R_2}{HO-C-CO_2H}}\overset{}{H}$ | Column III (structure with $R_1$, $R_2$, x) $R_1$ $R_2$ x | Column IV XII (structure) | Column V (structure) $R_1$ $R_2$ X |
|---|---|---|---|---|---|
| 45. | CH₃ | —CH₃ | | biphenyl-CH₂ variant | |
| 46. | H₃C—(CH₂)₅— | —H | | OCNH₂ variant | |
| 47. | phenyl-(CH₂)₄— | —CH₃ | | 4-fluorophenoxy variant | |
| 48. | phenyl- | —H | | phenyl-O-CH₂ variant | |

TABLE A-continued

| Ex. No. | Column I<br>$R_1-\overset{\overset{\displaystyle O}{\|}}{P}-Cl$<br>$\underset{Cl}{\|}$<br>$R_1$ | Column II<br>$\underset{R_2}{\overset{R_2}{\|}}$<br>$HO-\overset{\|}{C}-CO_2H$<br>$\underset{H}{\|}$<br>$R_2$ | Column III<br>$\overset{O}{\underset{\|}{P}}\overset{R_2}{\underset{\|}{\diagdown}}\overset{}{\underset{O}{\diagup}}\overset{}{\underset{\|}{C}}=O$<br>$R_1 \quad\quad\quad x$<br>$R_1 \quad R_2 \quad x$ | Column IV<br>XII | Column V<br>$\overset{\overset{\displaystyle O}{\|}}{R_1-P}-O-\overset{R_2}{\underset{\|}{C}}H-\overset{\overset{\displaystyle O}{\|}}{C}-X$<br>$\underset{OH}{\|}\quad\underset{R_2}{\|}$<br>$R_1 \quad\quad\quad X$ |
|---|---|---|---|---|---|
| 49. | ![phenyl-CH2-] | —CH₃ | | ![structure with phenoxy, N, COOC(CH3)3, (L), H] | |
| 50. | ![phenyl-(CH2)2-] | —CH₃ | | ![structure with phenoxy, N, COOC(CH3)3, (L), H] | |

What is claimed is:

1. A process for preparing a phosphonic acid intermediate which is a cyclic mixed anhydride of the structure

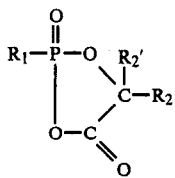

wherein $R_1$ is lower alkyl, aminoalkyl, haloalkyl, aryl, aralkyl, cycloalkyl or cycloalkylalkyl and $R_2$ is H, lower alkyl, aminoalkyl, aryl, aralkyl, cycloalkyl or cycloalkylalkyl and $R_{2'}$ is H, which comprises treating a phosphonic acid dichloride of the structure

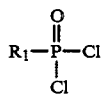

with an α-hydroxy acid of the structure

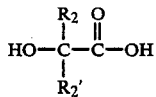

at a temperature within the range of from about $-85°$ C. to about $-65°$ C., employing a molar ratio of dichloride:acid of within the range of from about 3:1 to about 0.5:1 in the presence of an organic base, to form the cyclic mixed anhydride.

2. The process as defined in claim 1 wherein $R_1$ is aralkyl, and $R_2$ is aminoalkyl, phenyl, alkyl or phenylalkyl.

3. The process as defined in claim 1 wherein $R_1$ is $C_6H_5-(CH_2)_4-$, $R_{2'}$ is H or $CH_3$, and $R_2$ is $C_6H_5$, $C_6H_5-CH_2$, $CH_3$

or $-NHBOC-(CH_2)_4$, where in Z is

and BOC is $t-C_4H_9-O-CO-$.

4. A phosphonic acid intermediate having the structure

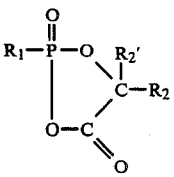

wherein $R_1$ is lower alkyl, aminoalkyl, haloalkyl, aryl, aralkyl, cycloalkyl or cycloalkylalkyl; $R_2$ is H, lower alkyl, aminoalkyl, aryl, aralkyl, cycloalkyl or cycloalkylalkyl; and $R_{2'}$ is H.

5. The intermediate as defined in claim 4 wherein $R_1$ is $C_6H_5-(CH_2)_4-$ and $R_2$ is $C_6H_5$, $C_6H_5CH_2$, $CH_3$, $-(CH_2)_4NHZ$ or $-(CH_2)_4NHBOC$, wherein Z is $C_6H_5CH_2OC$ and BOC is $t-C_4H_9OC$.

* * * * *

UNITED STATES PATENT AND TRADEMARK OFFICE
CERTIFICATE OF CORRECTION

PATENT NO. : 4,885,380

DATED : December 5, 1989

INVENTOR(S) : John K. Thottathil

It is certified that error appears in the above-identified patent and that said Letters Patent is hereby corrected as shown below:

In Claim 5, line 4, "$C_6H_5CH_2OC$" should read --$C_6H_5CH_2\underset{O}{OC}$-- and "$t-C_4H_9OC$" should read --$t-C_4H_9\underset{O}{OC}$--.

Signed and Sealed this

Ninth Day of October, 1990

Attest:

HARRY F. MANBECK, JR.

*Attesting Officer*  *Commissioner of Patents and Trademarks*